United States Patent
Gumennik et al.

(10) Patent No.: US 12,350,385 B2
(45) Date of Patent: Jul. 8, 2025

(54) TECHNOLOGIES FOR FIBER NANOTECHNOLOGY

(71) Applicant: THE TRUSTEES OF INDIANA UNIVERSITY, Bloomington, IN (US)

(72) Inventors: Alexander Gumennik, Bloomington, IN (US); Louis Alexandre Van Der Elst, Bloomington, IN (US); Merve Gokce, Bloomington, IN (US); Chandan K. Sen, Indianapolis, IN (US)

(73) Assignee: THE TRUSTEES OF INDIANA UNIVERSITY, Bloomington, IN (US)

( * ) Notice: Subject to any disclaimer, the term of this patent is extended or adjusted under 35 U.S.C. 154(b) by 470 days.

(21) Appl. No.: 17/771,293

(22) PCT Filed: Nov. 2, 2020

(86) PCT No.: PCT/US2020/058494
§ 371 (c)(1),
(2) Date: Apr. 22, 2022

(87) PCT Pub. No.: WO2021/087438
PCT Pub. Date: May 6, 2021

(65) Prior Publication Data
US 2022/0401616 A1    Dec. 22, 2022

Related U.S. Application Data

(60) Provisional application No. 62/928,658, filed on Oct. 31, 2019.

(51) Int. Cl.
*A61L 17/00* (2006.01)
*A61L 17/14* (2006.01)
(Continued)

(52) U.S. Cl.
CPC .......... *A61L 17/005* (2013.01); *A61L 17/145* (2013.01); *B21F 45/00* (2013.01); *D01D 5/00* (2013.01);
(Continued)

(58) Field of Classification Search
CPC ................. A61L 17/005; A61L 17/145; A61L 2300/104; A61L 2300/404; D01D 5/00;
(Continued)

(56) References Cited

U.S. PATENT DOCUMENTS

2006/0067621 A1    3/2006    Eves et al.
2006/0245702 A1    11/2006   Cazzini
(Continued)

OTHER PUBLICATIONS

Jayram et al., "Superhydrophobic Ag decorated ZnO nanostructured thin film as effective surface enhanced Raman scattering substrates." Applied Surface Science vol. 355, Nov. 15, 2015, pp. 969-977. (Year: 2015).*
(Continued)

*Primary Examiner* — Tan-Uyen T Ho
*Assistant Examiner* — Cherie M Poland
(74) *Attorney, Agent, or Firm* — Barnes & Thornburg, LLP

(57) ABSTRACT

Technologies for fibers with nanotechnology is disclosed. In the illustrative embodiment, a preform is 3D printed with one or more sacrificial cores and one or more hollow channels. The preform is drawn into a fiber, and one or more metal core(s) is inserted into the hollow channel during the fiber draw. The fiber is then heated, breaking up the sacrificial cores into balls through capillary action. The fiber can be etched, exposing the balls made up of the sacrificial cores. The balls can be selectively etched, exposing the metal core(s) of the fiber. Additional embodiments are disclosed.

16 Claims, 9 Drawing Sheets

(51) Int. Cl.
    *B21F 45/00*         (2006.01)
    *D01D 5/00*        (2006.01)
    *D02G 3/36*        (2006.01)
    *D02G 3/44*        (2006.01)
    *D06M 13/203*     (2006.01)
    *H01B 7/04*        (2006.01)
    *D06M 101/16*     (2006.01)

(52) U.S. Cl.
    CPC ............... *D02G 3/36* (2013.01); *D02G 3/448* (2013.01); *D02G 3/449* (2013.01); *D06M 13/203* (2013.01); *H01B 7/048* (2013.01); *A61L 2300/104* (2013.01); *A61L 2300/404* (2013.01); *D06M 2101/16* (2013.01); *D10B 2101/20* (2013.01); *D10B 2401/16* (2013.01); *D10B 2509/04* (2013.01)

(58) Field of Classification Search
    CPC .......... D02G 3/36; D02G 3/448; D02G 3/449; H01B 7/048; D06M 2101/16; D10B 2101/20; D10B 2101/16; D10B 2509/04
    See application file for complete search history.

(56) References Cited

U.S. PATENT DOCUMENTS

| | | | |
|---|---|---|---|
| 2014/0130350 A1 | | 5/2014 | Raymond |
| 2014/0212084 A1* | | 7/2014 | Gumennik ....... B29D 11/00721 |
| | | | 385/12 |
| 2018/0161005 A1 | | 9/2018 | Yamada |
| 2019/0038787 A1 | | 2/2019 | Ando |

OTHER PUBLICATIONS

Puca et al., Molecules. Jun. 2019; 24(12):2280. ePub Jun. 19, 2019 (PMC6630542) (Year: 2019).*

Zhou Li et al., (2014 Nanotechnology 25 145702 (8pp), published Mar. 12, 2014; doi:10.1088/0957-4484/25/14/145702). (Year: 2014).*

Supplementary European Search Report for counterpart EP Application No. 20881068.9, dated Feb. 11, 2023.

Jianhua et al., "Surgical Sutures with Porous Sheaths for the Sustained Release of Growth Factors", Advanced Materials, VCH Publishers, DE, vol. 28, No. 23, (Apr. 5, 2016), pp. 4620-4624, XP071816096, ISSN: 0935-9648, DOI: 10.1002/ADMA. 201506242.

PCT International Search Report and Written Opinion completed by the ISA/US on Feb. 5, 2021 and issued in connection with PCT/US2020/058494.

* cited by examiner

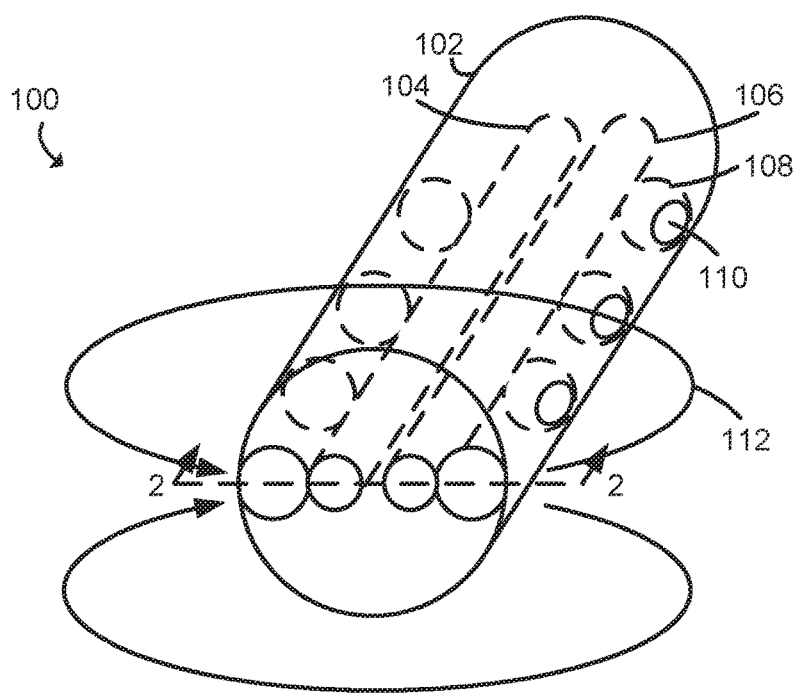
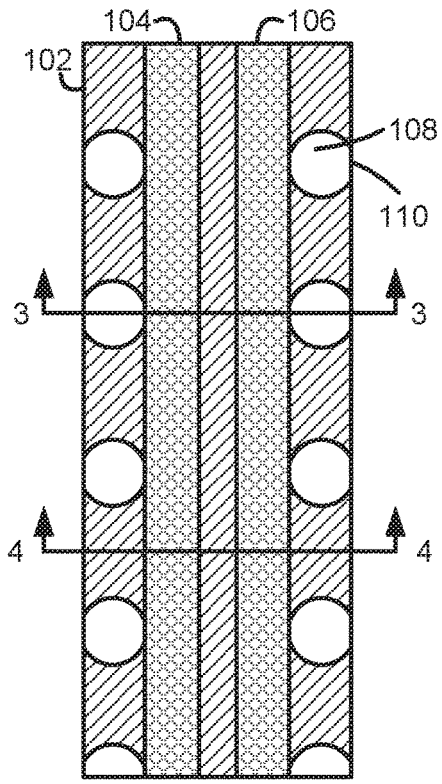
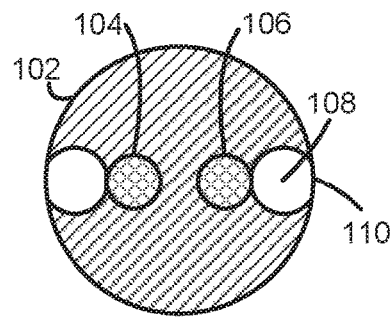
FIG. 3
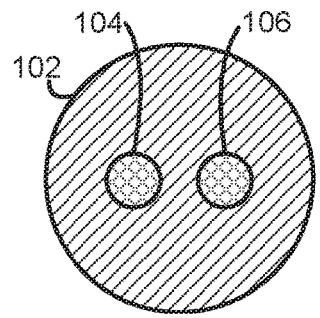
FIG. 4
FIG. 1
FIG. 2

TECHNOLOGIES FOR FIBER NANOTECHNOLOGY

CROSS-REFERENCE TO RELATED APPLICATIONS

This application is a U.S. national counterpart application of international application serial No. PCT/US2020/058494 filed Nov. 2, 2020, which claims the benefit of U.S. Provisional Patent Application No. 62/928,658, entitled "Suture Fiber Nanotechnology Device" and filed on Oct. 31, 2019. The disclosures 62/928,658 and PCT/US2020/058494 are expressly incorporated by reference in their entireties.

BACKGROUND

Fibers may be used in medical procedures, such as being used as sutures. Typical sutures perform the function of keeping a wound closed, but do not aid healing beyond that function.

Bacterial infections in wounds can worsen a patient's condition. Electric fields can disrupt formation of bacterial films, but applying a suitable electric field to at a wound can be challenging.

SUMMARY

The present disclosure may comprise one or more of the following features and combinations thereof.

According to one aspect of the disclosure, a fiber comprises a first core extending along an axis of the fiber; a second core extending along the axis of the fiber different from the first core; a cladding surrounding the first core and the second core; wherein the cladding has a plurality of outlets spaced-apart along the axis of the fiber, wherein each outlet of the plurality of outlets exposes a of the first core or the second core to an environment surrounding the fiber, wherein the first core and the second core generate an electric field in the environment surrounding the fiber.

In some embodiments, the first core and the second core generate an electric field in the environment surrounding the fiber based on an electrochemical interaction between the first core and the second core.

In some embodiments, the first core is zinc and the second core is silver.

In some embodiments, an external voltage source is applied across the first core and the second core to generate the electric field.

In some embodiments, the cladding is polycarbonate.

In some embodiments, the fiber is used as a suture in a wound of a patient.

In some embodiments, the electric field is at least ten millivolts per millimeter.

According to one aspect of the disclosure, a fiber comprises a biocompatible polymer cladding; a biocompatible coating surrounding the biocompatible polymer cladding, the biocompatible coating configured to dissolve in a wound environment; wherein the biocompatible polymer cladding has a pneumatic or fluidic channel with one or more outlets from the pneumatic or fluidic channel to the biocompatible coating, wherein the fiber has a length of at least 10 millimeters and a diameter less than one millimeter.

In some embodiments, the pneumatic or fluidic channel has a drug therein to be delivered to a patient.

In some embodiments, the pneumatic or fluidic channel has a tissue sample that been sampled from a patient.

In some embodiments, the fiber comprises a first core and a second core that generate an electric field in the environment surrounding the fiber based on an electrochemical interaction between the first core and the second core.

In some embodiments, the electric field is at least ten millivolts per millimeter.

In some embodiments, the first core is zinc and the second core is silver.

In some embodiments, the fiber comprises a first core and a second core, wherein an external voltage source is applied across the first core and the second core to generate the electric field.

In some embodiments, the biocompatible polymer cladding is polycarbonate.

In some embodiments, the fiber is used as a suture in a wound of a patient.

According to one aspect of the disclosure, a method of manufacturing a fiber comprises creating a preform, wherein the preform comprises one or more sacrificial cores; drawing the preform into a fiber; annealing the fiber after drawing the fiber; after annealing the fiber, heating the fiber to break up the sacrificial core by capillary action into a plurality of balls; etching the fiber to expose the plurality of balls; and etching the plurality of balls.

In some embodiments, drawing the preform into a fiber comprises inserting one or more metal wires into the preform and drawing the metal wires along with the fiber to create a fiber with one or more metal cores.

In some embodiments, creating the preform comprises 3D printing the preform.

In some embodiments, the preform has a hollow channel and drawing the preform into a fiber comprises drawing the preform into a fiber with a hollow channel.

BRIEF DESCRIPTION OF THE DRAWINGS

The detailed description particularly refers to the accompanying figures in which:

FIG. 1 is a perspective view of one embodiment of a fiber;

FIG. 2 is a longitudinal cross-section of the fiber of FIG. 1;

FIG. 3 is a transverse cross-section of the fiber of FIG. 1;

FIG. 4 is a transverse cross-section of the fiber of FIG. 1;

DETAILED DESCRIPTION OF THE DRAWINGS

Figure 5:
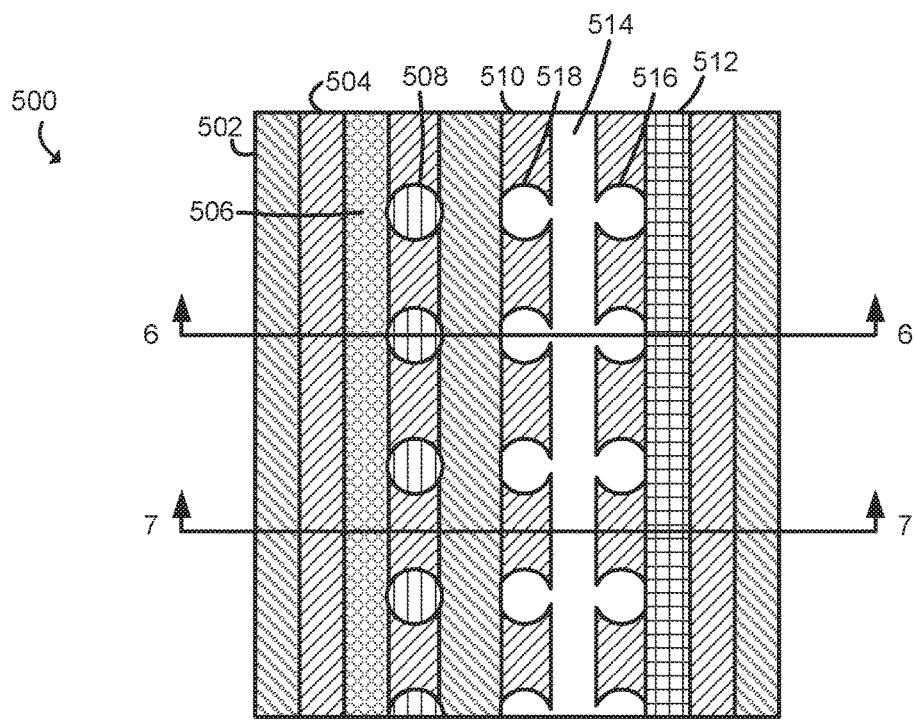
FIG. 5 is a longitudinal cross-section of one embodiment of a fiber.

Terms used throughout this application are to be construed with ordinary and typical meaning to those of ordinary skill in the art. However, Applicant desires that the following terms be given the particular definition as defined below.

As used in the specification and claims, the singular form "a," "an," and "the" include plural references unless the context clearly dictates otherwise. For example, the term "a cell" includes a plurality of cells, including mixtures thereof.

The terms "about" and "approximately" are defined as being "close to" as understood by one of ordinary skill in the art. In one non-limiting embodiment the terms are defined to be within 10%. In another non-limiting embodiment, the terms are defined to be within 5%. In still another non-limiting embodiment, the terms are defined to be within 1%.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

An "effective amount" is an amount sufficient to effect beneficial or desired results. An effective amount can be administered in one or more administrations, applications or dosages. The term "carrier" or "pharmaceutically acceptable carrier" means a carrier or excipient that is useful in preparing a pharmaceutical or therapeutic composition that is generally safe and non-toxic, and includes a carrier that is acceptable for veterinary and/or human pharmaceutical or therapeutic use. As used herein, the terms "carrier" or "pharmaceutically acceptable carrier" encompasses can include phosphate buffered saline solution, water, emulsions (such as an oil/water or water/oil emulsion) and/or various types of wetting agents. As used herein, the term "carrier" encompasses any excipient, diluent, filler, salt, buffer, stabilizer, solubilizer, lipid, stabilizer, or other material well known in the art for use in pharmaceutical formulations and as described further below.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed.

The terms "therapeutically effective amount" or "therapeutically effective dose" refer to the amount of a composition, such as glucose-modified insulin bound to a glucose-binding structure, that will elicit the biological or medical response of a tissue, system, animal, or human that is being sought by the researcher, veterinarian, medical doctor or other clinician over a generalized period of time. In some instances, a desired biological or medical response is achieved following administration of multiple dosages of the composition to the subject over a period of days, weeks, or years.

The term "subject" or "recipient" is defined herein to include animals such as mammals, including, but not limited to, primates (e.g., humans), cows, sheep, goats, horses, dogs, cats, rabbits, rats, mice and the like. In some embodiments, the subject is a human.

The terms "treat," "treating," "treatment," and grammatical variations thereof as used herein, include partially or completely delaying, alleviating, mitigating or reducing the intensity of one or more attendant symptoms of a disorder or condition and/or alleviating, mitigating or impeding one or more causes of a disorder or condition. Treatments according to the invention may be applied preventively, prophylactically, palliatively, or remedially.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring now to FIGS. 1-4, in one embodiment, a fiber 100 has a cladding 102 surrounding a first core 104 and a second core 106. The cladding 102, the first core 104, and the second core 106 extend along an axis of the fiber. The cladding 102 keeps the first core 104 separate from the second core 106. The fiber 100 has several holes 108 spaced out along the axis of the fiber 100, forming several outlets 110. Each outlet 110 exposes the first core 104 or the second core 106 to the environment of the fiber 100. In the illustrative embodiment, an electric field 112 is created between the first core 104 and the second core 106, such as by application of an external voltage across the cores 104, 106 or by an electrochemical interaction. In use, in the illustrative embodiment, some or all of the fiber 100 may be in contact with a patient. For example, the fiber 100 may be used a suture to close a wound in a patient. It should be appreciated that, in such embodiments, the electric field 112 may disrupt formation of a bacterial biofilm, improving the healing of the wound.

In the illustrative embodiment, the cladding 102 is a biocompatible polycarbonate. Additionally or alternatively, the cladding 102 could be any suitable material that is capable of performing as described herein, including being capable of being drawn into a fiber and being compatible with a capillary breakup of a sacrificial core, described in more detail below.

In the illustrative embodiment, the first core 104 and second core 106 are two different metals, with an electrochemical voltage established between them. For example, the first core 104 can be zinc, and the second core 106 can be silver, creating a voltage of about 1.5 volts between the first core 104 and the second core 106. The surrounding liquid may act as a bridge electrons to travel from the silver core to the zinc core, creating an electric current. The corresponding field strength may be, e.g., 0.1-10 volts per millimeter. In other embodiments, different conductors can be used, establishing different voltage levels between the cores 104, 106. For example, the first core 104 could be any of magnesium, magnesium alloys, beryllium, galvanized steels, aluminum, zinc, zinc alloys, cadmium, iron, cobalt, tungsten, or chromate, and the second core 106 could be any of gold, palladium, gold-platinum alloy, rhodium-plated copper, platinum, silver, silver-plated copper, nickel-copper alloys, nickel, titanium, titanium alloys, copper, copper-tin alloys, copper-zinc alloys, silver, silver alloys, chromium-plated steels, or tin-plated metals. More generally, any set of cores described herein may be any combination of any of the materials listed above. Additionally or alternatively, in some embodiments, a function generator, battery, or other voltage source may be applied across the first core 104 and the second core 106. It should be appreciated that, in such embodiments, the first core 104 and the second core 106 may be the same material, such as copper or another conductive material. In the illustrative embodiment, the illustrative first core 104 and second core 106 may follow a helical path along the fiber, with the first core 104 forming a twisted pair with the second core.

The fiber 100 may be any suitable size. For example, the diameter of the fiber 100 may be any size from, e.g., 1 micrometer to 1,000 micrometers, and the length of the fiber 100 may be any suitable length, such as 1 millimeter to 100 meters. The diameter of each core 104, 106 may be any suitable size, such as 200 nanometers to 300 micrometers. The diameter of each hole 108 may be any suitable size, such as 200 nanometers to 200 micrometers. The diameter of each outlet 110 may be any suitable size, such as 20 nanometers to 200 micrometers. In the illustrative embodiment, the fiber 100 has a diameter of 200-400 micrometers, each core 104, 106 has a diameter of 50-100 micrometers, and each of the holes 108 has a diameter of 20-50 micrometers.

Figure 6:
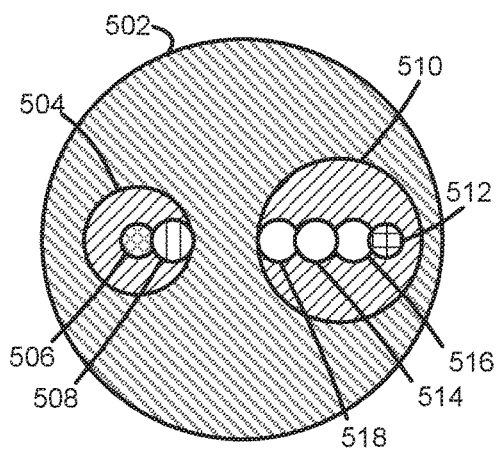
FIG. 6 is a transverse cross-section of the fiber of FIG. 5.
Figure 7:
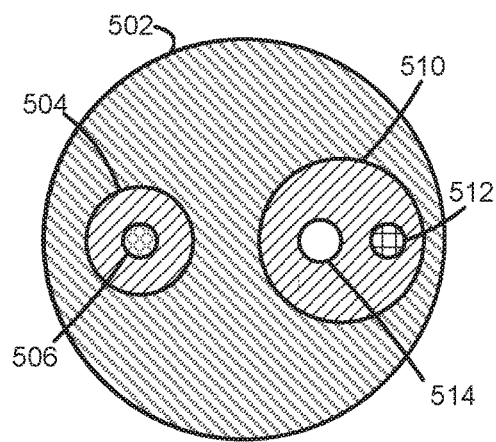
FIG. 7 is a transverse cross-section of the fiber of FIG. 5.

Referring now to FIGS. 5-7, in one embodiment, a fiber 500 has an outer cladding 502 surrounding a first inner cladding 504 and a second inner cladding 510. The first inner cladding 504 surrounds a first core 506, and the second inner cladding 510 surrounds a second core 512 and a hollow core 514. The outer cladding 502, the first inner cladding 504, the first core 506, the second inner cladding 510, the second core 512, and the hollow core 514 extend along an axis of the fiber. The outer cladding 502 keeps the first inner cladding 504 separate from the second inner cladding 510, the first inner cladding 504 keeps the first core 506 separate from the outer cladding 502 and the second inner cladding 510, and the second inner cladding 510 keeps the second core 514 and the hollow core 514 separate from the outer cladding 502 and the first inner cladding 504. Additionally, the second inner cladding 510 keeps the second core 514 separate from the hollow core 514.

Several conductive balls 508 are spaced out axially along the fiber 500. Each of the conductive balls 508 is in contact with the first core 506 and extends through the first inner cladding 504 to the outer cladding 502. In use, in some embodiments, the outer cladding 502 can be partially or completely removed, allowing each conductive ball 508 to electrically couple the first core 506 to the surrounding environment.

The fiber 500 has several holes 516 and several holes 518 spaced out along the axis of the fiber 500. Each hole 516 extends from the second core 512, through the second inner cladding 510, and to the hollow core 514. Each hole 518 extends from the hollow core 514, through the second inner cladding 510, and to the outer cladding 502. In use, in some embodiments, the outer cladding 502 can be partially or completely removed, allowing the holes 516 to expose the second core 512 to the hollow core 514 and to the environment of the fiber 500, and allowing the holes 518 to expose the hollow core 514 to the environment of the fiber 500. In the illustrative embodiment, an electric field is created between the first core 506 and the second core 512 in a similar manner as the electric field 112.

A drug may be administered by allowing it to flow through the hollow core 514 and the holes 518 into a patient in locations where the outer cladding 502 is removed. In some embodiments, an electric field may be applied (e.g., by applying a voltage across first core 506 and second core 512) to cause electroporation of tissue cells and facilitate the flow of the drug to the desired location. Additionally or alternatively, in some embodiments, the drug itself may propagate with the electric field by electrophoresis. In some embodiments, instead of delivering drugs, the hollow core 514 may be used to extract a sample from a patient, such as extracellular fluid, vesicles, etc., or the fiber 500 may integrate devices for monitoring tissue environment such as temperature, pH, etc.

The voltage applied across the first core 506 and the second core 512 may be any suitable voltage, such as 0.1-30,000 volts, with a corresponding electric field of, e.g., 1-1,000 volts per centimeter. In the illustrative embodiment, the electric field may cause electroporation in some or all of the cells in the area of the electric field, temporarily creating nanopores in the cells and causing the drug to flow into the cells by, e.g., electrophoresis or diffusion or fluidic force. In some embodiments, the electric field may be pulsed. For example, in the illustrative embodiment, the electric field may be applied in ten pulses of 100 milliseconds for each pulse. In some embodiments the pulses may have a different amplitude. For example, the amplitude of each pulse may be lower than that of the previous pulse. The pulses may be applied for any suitable length of time, such as 10-1,000 milliseconds, and may be repeated for any suitable number of times, such as 1-30 times, and may have any suitable time between pulses, such as 10-1,000 milliseconds.

It should be appreciated that the width of the hollow core 514 and/or the holes 516, 518 may be varied such that certain drugs, such as genes, DNA, or protein, can be administered at a desired rate. Additionally, the drugs may be administered to a variety of different depths, based on the positioning of the fiber 500, the hollow core 514, and the holes 516, 518. In the illustrative embodiment, there is a hollow core 514. Additionally or alternatively, in some embodiments, there may be more than one hollow core 514.

It should be appreciated that the different hollow cores 514 may have be used to deliver different drugs. In some embodiments, different hollow cores 514 on the same fiber 500 may have different diameters.

The drug may be inserted into the hollow core 514 in any suitable manner. For example, in the illustrative embodiment, the hollow core 514 may be connected to a syringe with use of a tube running from the syringe to a block (such as polydimethylsiloxane) that is coupled to an opening of the hollow core 514. In some embodiments, the syringe may be embedded in or form a part of a handpiece. The handpiece and syringe may be removably connected to the fiber 500 such that the fiber 500 may be discarded after a single use and the handpiece and syringe may be reused.

As used herein, the terms "drug" or "drug formulation" are used broadly to refer to any prophylactic, therapeutic, diagnostic, or theranostic agent, or other substance that may be suitable for introduction to biological tissues, including pharmaceutical excipients and substances for tattooing, cosmetics, and the like. The drug can be an agent having biological activity. The drug formulation may include various forms, such as liquid solutions, gels, solid particles (e.g., microparticles, nanoparticles), or combinations thereof. The drug may comprise small molecules, large (i.e., macro-) molecules, or a combination thereof. In representative, not non-limiting, embodiments, the drug can be selected from among amino acids, vaccines, antiviral agents, gene delivery vectors, interleukin inhibitors, immunomodulators, neurotropic factors, neuroprotective agents, antineoplastic agents, chemotherapeutic agents, polysaccharides, anti-coagulants, antibiotics, analgesic agents, anesthetics, antihistamines, anti-inflammatory agents, and viruses. The drug may be selected from suitable proteins, peptides and fragments thereof, which can be naturally occurring, synthesized or recombinantly produced. In one embodiment, the drug formulation includes insulin. The drug formulation may further include one or more pharmaceutically acceptable excipients, including pH modifiers, viscosity modifiers, and diluents.

It should be appreciated that the fiber 500 may be used on the skin (or parts thereof), across the blood-brain barrier, mucosal tissue (e.g., oral, nasal, ocular, vaginal, urethral, gastrointestinal, respiratory), blood vessels, lymphatic vessels, cell membranes (e.g., for the introduction of material into the interior of a cell or cells), or other biological tissue or barrier. The biological barriers may be in humans or other types of animals, as well as in plants, insects, or other organisms, including bacteria, yeast, fungi, and embryos. Additionally, the fiber 500 may be applied to tissue internally with the aid of a catheter, endoscope, laparoscope, etc. For certain applications, such as for a drug delivery to an internal tissue, a device with the fiber 500 may be surgically implanted or integrated into surgical tools.

In the illustrative embodiment, the outer cladding 502 is made of a material that will dissolve in the environment of a wound. For example, the outer cladding 502 may be made of a material that dissolves in the higher pH environment of a wound. It should be appreciated that, in such an embodiment, only the outer cladding 502 that is in the environment of a wound will dissolve, allowing any medication or tissue sampling delivered through the hollow core 514 to be focused on the wounded area. Each of the first inner cladding 504 and the second inner cladding 510 may be made of the same or a similar material as the cladding 102 described above.

Each of the conductive balls 508 may be embodied as a suitable material. In the illustrative embodiment, each of the conductive balls 508 is embodied as a cyclic-olefin copolymer doped with carbon nanotubes or carbon-black (graphite) particles. The first core 506 and the second core 512 may be the same as or similar to the first core 104 and the second core 106 described above.

The fiber 500 may be any suitable size. For example, the diameter of the fiber 500 may be any size from, e.g., 4 micrometer to 4,000 micrometers, and the length of the fiber 500 may be any suitable length, such as 1 millimeter to 100 meters. The diameter of each inner cladding 504, 510 may be any suitable diameter, such as 1 micrometer to 4,000 micrometers. The diameter of each core 506, 512, 514 may be any suitable size, such as 200 nanometers to 300 micrometers. The diameter of each conductive all 508, each hole 516, or each hole 518 may be any suitable size, such as 200 nanometers to 200 micrometers.

It should be appreciated that the present disclosure is not limited to the embodiments described in FIGS. 1-7. Rather, different combinations of the features disclosed in those embodiments are envisioned as well. For example, various embodiments may include different types or quantities of cores, different arrangement of outlets, etc. In one embodiment, for example, a fiber may include the second inner cladding 510 and its inner components (i.e., the second core 512, the hollow core 514, the holes 516, and the holes 518) without the outer cladding 502, the first inner cladding 504, or the inner components of the first inner cladding 504. In some embodiments, the fiber can embed sensors and transducers for optical, electrical, mechanical, and chemical sensing and stimuli. In case of implantation into biological tissue, the fiber can use the living tissue filling the space between the electrodes as a component of a sensor/transducer device.

Figure 8:
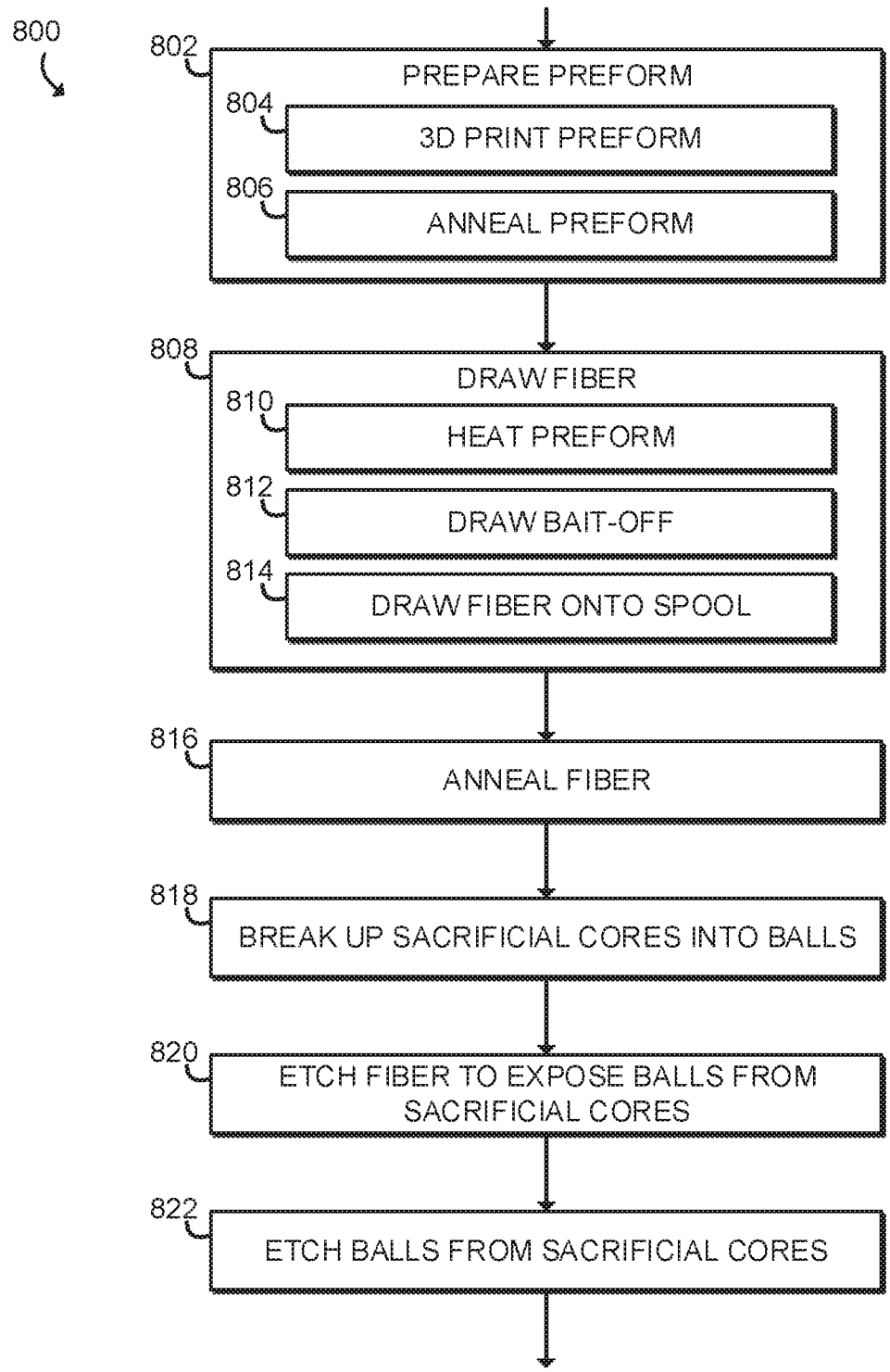
FIG. 8 is a simplified flow diagram of at least one embodiment of a method for manufacturing the fibers of FIGS. 1-7.
Figure 9:
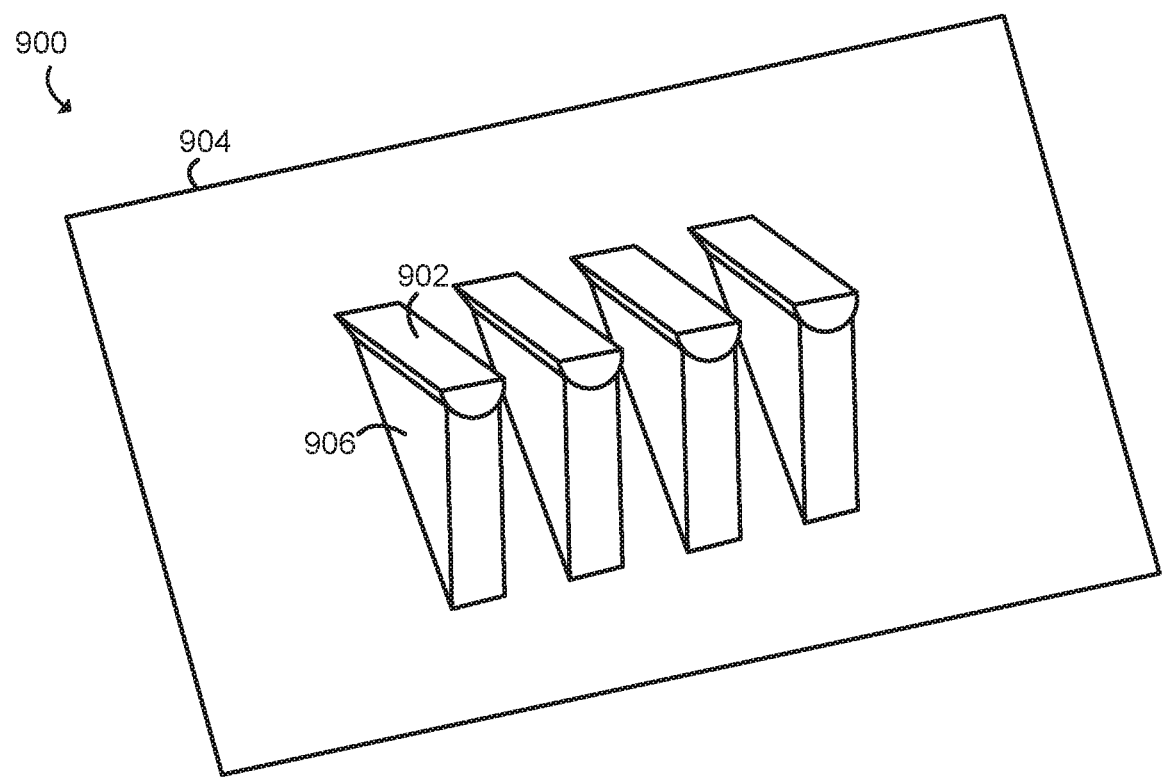
FIG. 9 is a perspective view of one embodiment of a 3D-printed preform.

Referring now to FIG. 8, in use, a method 800 for manufacturing a fiber (such as the fiber 100, 500) is disclosed. The method begins in block 802, in which a preform is prepared. In the illustrative embodiment, a preform is 3D printed in block 804. As shown in FIG. 9, in the illustrative embodiment, a partial preform 902 may be 3D printed on a substrate 904 at an angle, with support structure 906 supporting the partial preform 902 as it is being printed. The angle of the substrate 904 may be, e.g., 30-60 degrees, which can affect the success of the 3D printing. It should be appreciated that, in some embodiments, the partial preform 902 or a complete preform may be printed at a different orientation, such as printed upright in full (instead of a half). The support structure 906 may be a different material from the partial preform 902 and may be removable from the partial preform 902. The partial preform 902 may be made of any one or more suitable materials. For example, in the illustrative embodiment, the partial preform 902 may have a cladding of polycarbonate and one or more sacrificial cores made up of a different material. The sacrificial cores may be any suitable material that will undergo capillary breakup without destroying the rest of the fiber, as described in more detail below. In the illustrative embodiment, the sacrificial cores are made of cyclo-olefin copolymer. It should be appreciated that the partial preform 902 may include one or more hollow channels or cores. The preforms may also undergo additional processing, such as by being cleaned in multiple washing cycles. In the illustrative embodiment, no washing cycle is used.

It should be appreciated that, in some embodiments, the preform may be created from a process other than 3D printing, such as any suitable subtractive and/or additive manufacturing techniques.

In block 806, the preform is annealed. For example, in the illustrative embodiments, two partial preforms 902 that are half cylinders are combined to form one complete preform. Annealing the preform can densify the polymer to soften each printed layer as a one void-free part. In the illustrative embodiment, the polycarbonate preform is heated up between 165° C. and 185° C. in an oven under vacuum for a suitable amount of time, such as 4-24 hours. The temperature of the oven may depend on the composition of the preform, including the compositions of cores in the preform. For example, a cyclo-olefin copolymer core may be annealed at around 174° C. The illustrative consolidation temperature is higher than the glass transition temperature of polycarbonate and less than its melting temperature. In some embodiments, the outer and inner structure of the preform are preserved in a polytetrafluoroethylene (PTFE) mold and hollow cores by PTFE filaments. Additionally or alternative, in some embodiments, high temperature resistant tape may be used to preserve the outer geometry. In some embodiments, the preform may be periodically rotated in the oven to ensure even annealing, such as every 5 to 8 hours.

Figure 10:
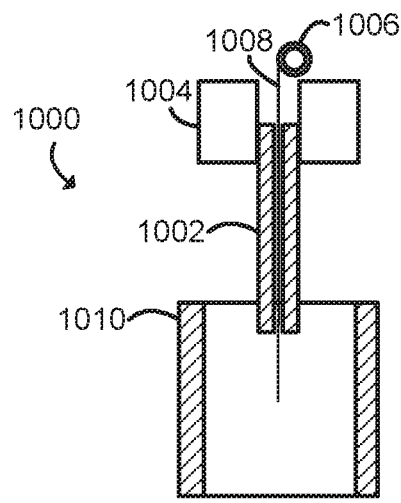
FIG. 10 is a cross-sectional view of a preform being inserted into a fiber drawing system.
Figure 11:
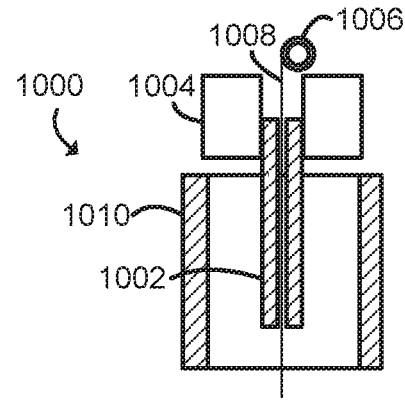
FIG. 11 is a cross-sectional view of a preform being heated in a fiber drawing system.
Figure 12:
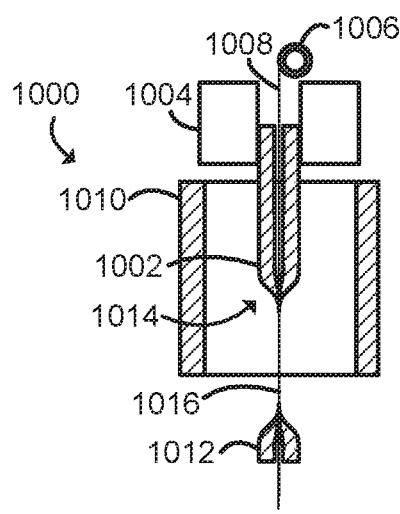
FIG. 12 is a cross-sectional view of a beginning of a fiber draw in a fiber drawing system.
Figure 13:
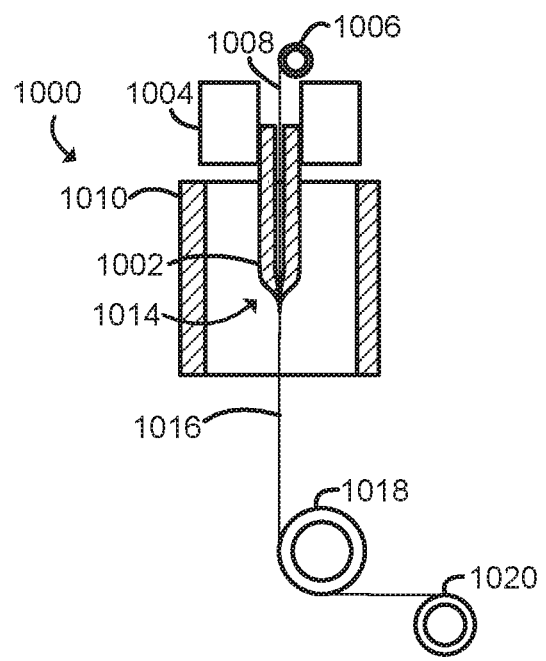
FIG. 13 is a cross-section view of a fiber draw in a fiber drawing system.
Figure 14:
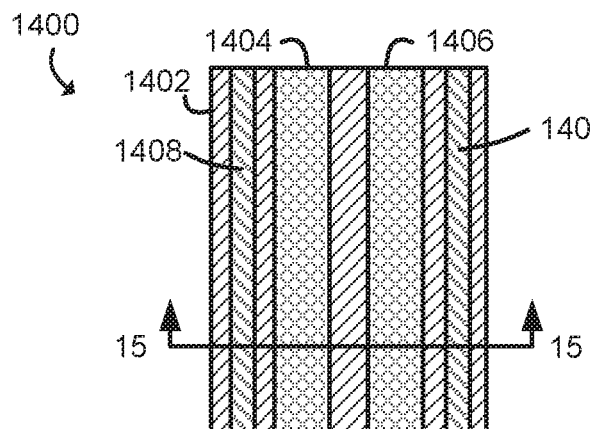
FIG. 14 is a longitudinal cross-section view of a fiber undergoing capillary breakup.
Figure 14:
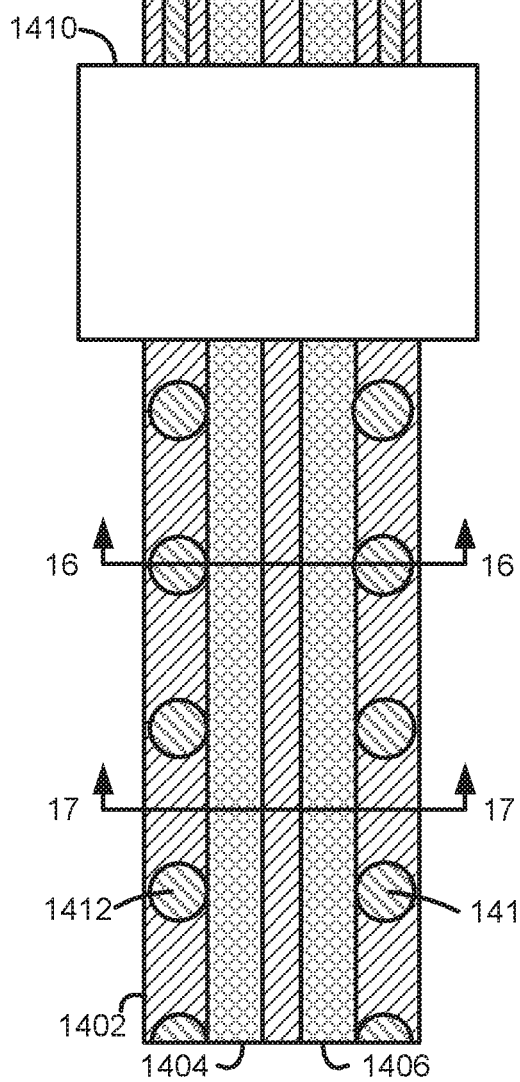

In block 808, the fiber is drawn, as shown in FIGS. 10-13. FIG. 10 shows a fiber draw system 1000, which includes a fiber preform 1002, a preform holder 1004, a wire 1008, a wire spool 1006, and a heater 1010. The wire 1008 may be any suitable material or thickness, such as the same or similar material as the first core 104 or the second core 106. It should be appreciated that, in some embodiments, more than one wire and wire spool may be included, such as for embodiments with more than one metal core. In the embodiment shown in FIGS. 10-13, the preform has a single hollow core that is to be filled with the wire 1008. The wire 1008 is passed through the hollow core of the preform, extending out the bottom as shown in FIG. 10.

In block 810, the preform 1002 is inserted into the heater 1010 and heated up. As the end of the preform heats up at the hottest part of the oven, a piece called the bait-off 1012 drops off the preform, forming a tapering region 1014 where the preform 1002 tapers to a fiber 1016. The bait-off 1012 is dawn off in block 812. In block 814, the fiber 1016 is drawn onto a capstan 1018 and spooled onto a spool 1020. It should be appreciated that, in the illustrative embodiment, the hollow core of the preform 1002 collapses around the wire 1008, forming a fiber with one or more metal wire cores. It should also be appreciated that the structure of the preform will generally be maintained as it is drawn down to a narrower diameter. For example, a hollow core (without a wire in it) may remain a hollow core and a sacrificial core may remain in place as a sacrificial core. In the illustrative embodiment, a wire 1008 that is zinc may have a diameter of at least 75 micrometers, and a wire 1008 that is copper or silver may have a diameter of at least 100 micrometers.

It should be appreciated that the parameters for the fiber draw system 1000 may depend on various factors, such as the number of cores, the diameter(s) of the wire(s) 1008, the materials used, etc. In the illustrative embodiment, the over set to a temperature of 260° C. The heater 1010 may be allowed to overshoot the set temperature and stabilize to the desired temperature. Tension may be placed on the bait-off 1012, such as by adding weights on the bait-off 1012, such as 25 to 50 gram weights. After the fiber 1016 is placed on the capstan 1018 and the fiber spool 1020, tension may be placed on the fiber 1016 by the capstan 1018 and/or the fiber spool 1020. Parameters of the fiber such as the diameter of the fiber 1016 may be monitored and used as feedback in controlling parameters of the fiber draw system 1000, such as the tension on the fiber 1016 and/or the temperature of the heater 1010. For example, if the diameter of the fiber 1016 is larger than desired, the tension (and spooling rate) of the fiber 1016 may be increased, which will decrease the diameter of the fiber 1016.

In block 816, the fiber is annealed. During the draw process, the polymer chains of the preform may align in the stretching direction, resulting in increased elastic modulus and tensile strength and reduced ductility in that direction. Annealing following the draw process decreases this alignment and increases the ductility, comparable to the known thermal treatment for metals. The fiber drawing may elongate amorphous regions of the polymer and align the crystalline regions along the stretching direction which may create internal stresses, especially in the amorphous region. Without annealing, such a fiber may shrink or curl when exposed to the temperatures necessary to induce capillary breakup of a sacrificial core. In the illustrative embodiment, annealing is done by placing the fiber in an oven under vacuum for 4 hours to 24 hours at 120° C.

Figure 15:
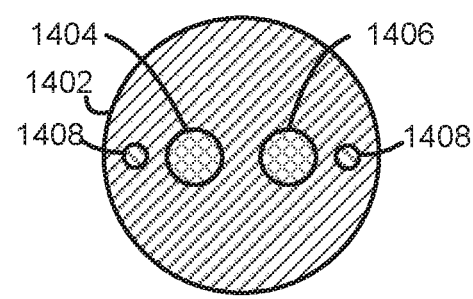
FIG. 15 is a transverse cross-section view of a fiber prior to the capillary breakup of FIG. 14.
Figure 16:
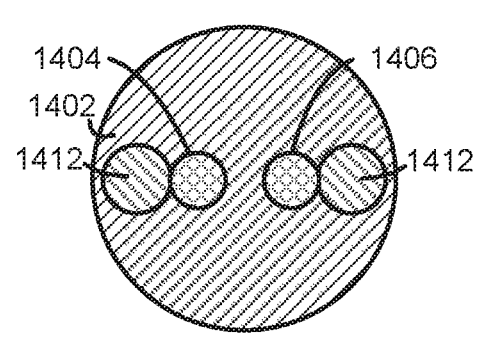
FIG. 16 is a transverse cross-section view of a fiber after the capillary breakup of FIG. 14.
Figure 17:
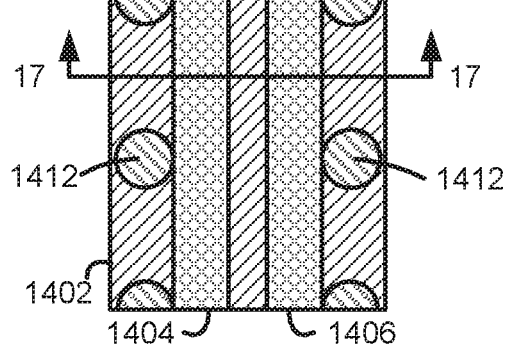
FIG. 17 is a transverse cross-section view of a fiber after the capillary breakup of FIG. 14.

In block 818, the sacrificial cores of the fiber are broken up through capillary action into balls. For example, as shown in FIGS. 14-17, in one embodiment, a fiber 1400 that has gone through the drawing and annealing process may have a cladding 1402, a first core 1404, a second core 1406, and two sacrificial cores 1408. As noted above, in the illustrative embodiment, the sacrificial cores 1408 are cyclic olefin copolymer. Before breakup, the sacrificial cores 1408 extend along the axis of the fiber 1400, similar to the cores 1404, 1406, as shown in FIG. 15 and the top portion of FIG. 14. The fiber 1400 is heated, such as by passing through a heating element 1410. The fiber 1400 is heated to a temperature of approximately 195° C. The heating element softens the sacrificial core 1408 and the surrounding cladding 1402, allowing the sacrificial core 1408 to break up into several balls 1412. In other embodiments, the fiber 1400 may be heated to a different temperature, depending on the materials used in the fiber 1400. For example, the fiber 1400 may be heated to any suitable temperature from 165 to 240° C. The diameter of the sacrificial cores 1408 and the mass of the cladding 1402 around the sacrificial cores 1408 affect the ability of the sacrificial cores 1408 to break up. In the illustrative embodiment, the ratio of the diameter of the cladding 1402 to the diameter of the sacrificial cores 1408 is at least 7:1 to ensure the sacrificial cores 1408 break up. After passing through the heating element 1410, the sacrificial cores 1408 have broken up into balls 1412, as shown in FIGS. 16 & 17 and the bottom half of FIG. 14.

Figure 18:
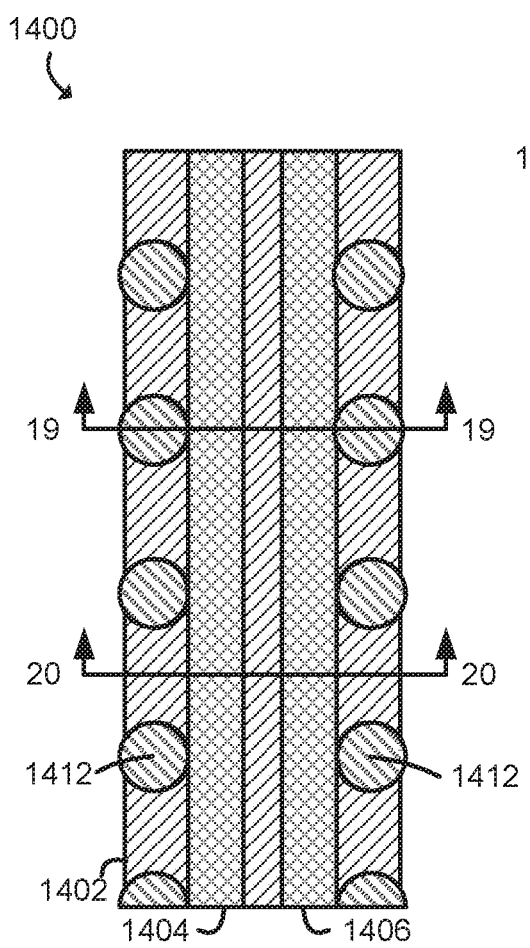
FIG. 18 is a longitudinal cross-section view of a fiber after capillary breakup and etching.
Figure 19:
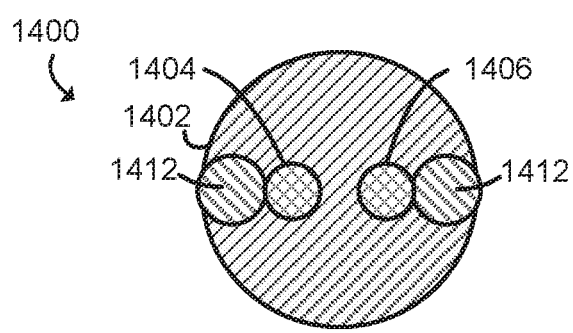
FIG. 19 is a transverse cross-section view of a fiber after etching.
Figure 20:
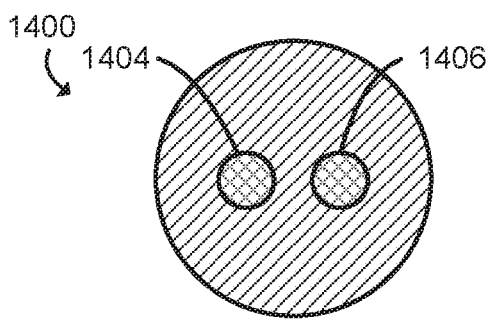
FIG. 20 is a transverse cross-section view of a fiber after etching.

In block 820, the cladding 1402 of the fiber 1400 is etched to expose the balls 1412, as shown in FIGS. 18-20. Any suitable etching substance may be used. In the illustrative embodiment, toluene diluted in dimethyl sulfoxide is used to etch the polycarbonate cladding 1402. The etching may be done by immersion and on a vortex mixer, such that decomposed polymeric material removes itself from the surface of the fiber 1400.

In block 822, the balls 1412 from the sacrificial cores 1408 can be etched away. In the illustrative embodiment, oleic acid is used to remove the balls 1412 made of cyclic-olefin copolymer, leaving a fiber 1400 with the same or a similar structure as the fiber 100 discussed above.

Figure 21:
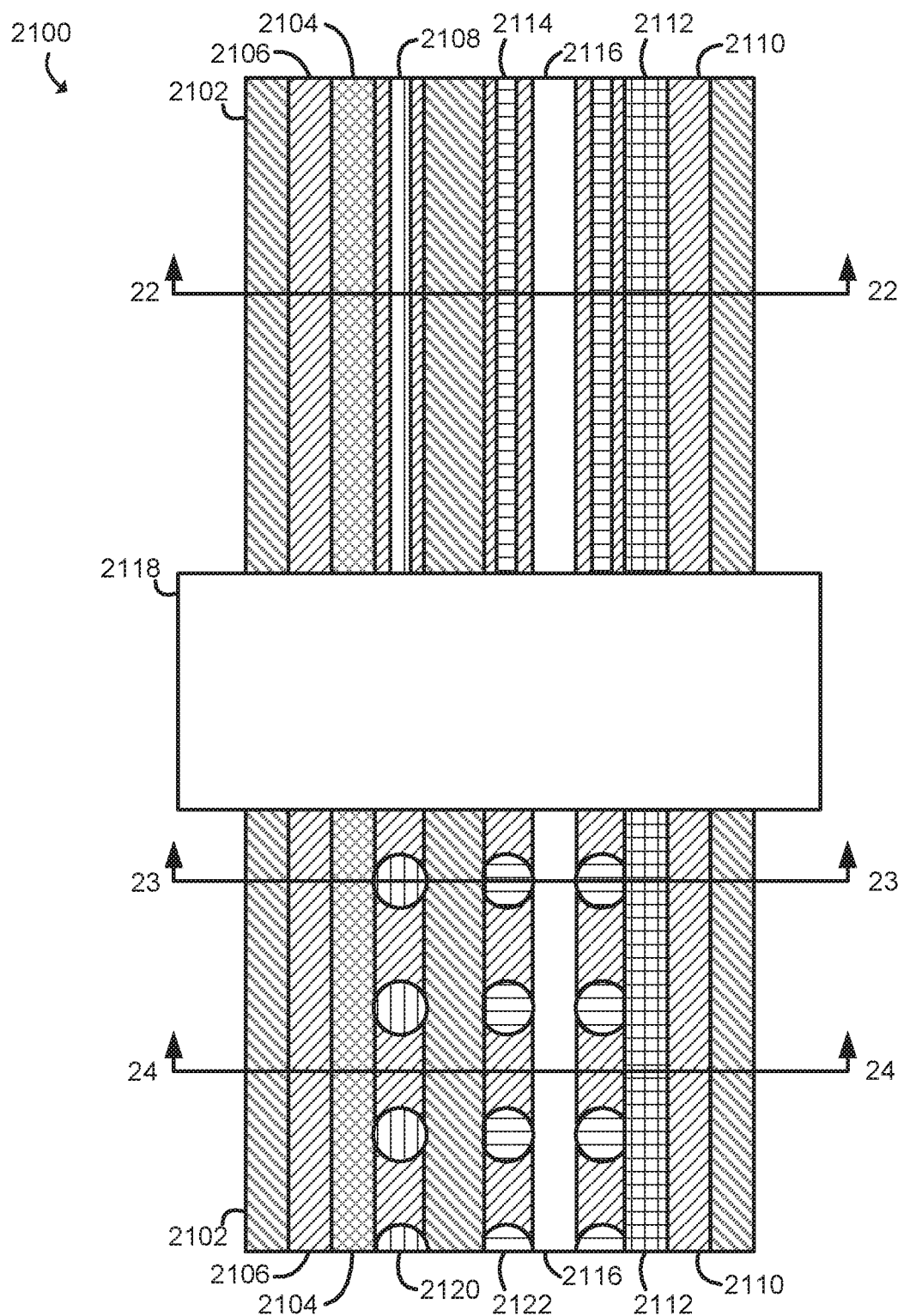
FIG. 21 is a longitudinal cross-section view of a fiber undergoing capillary breakup.
Figure 22:
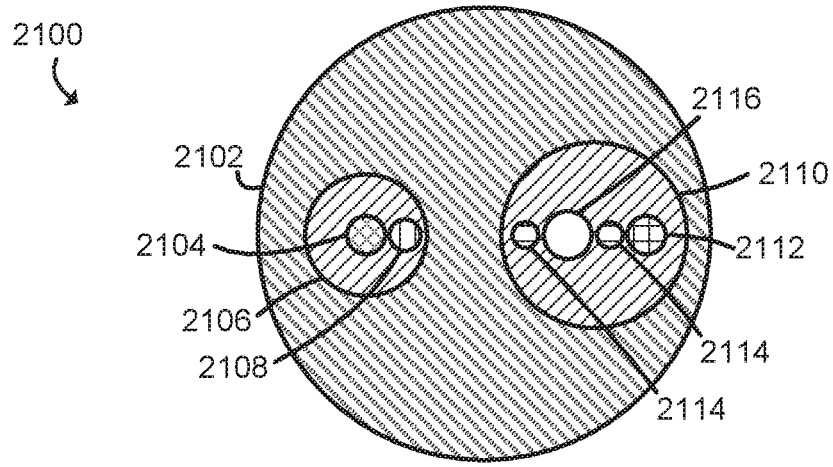
FIG. 22 is a transverse cross-section view of a fiber prior to the capillary breakup of FIG. 21.
Figure 23:
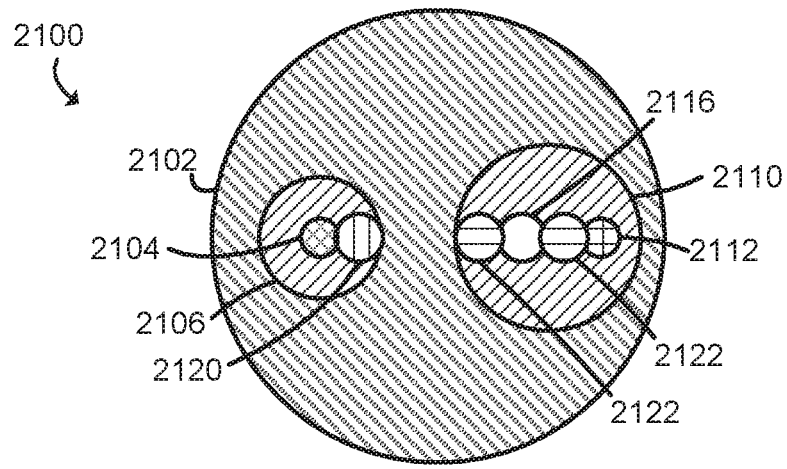
FIG. 23 is a transverse cross-section view of a fiber after the capillary breakup of FIG. 21.
Figure 24:
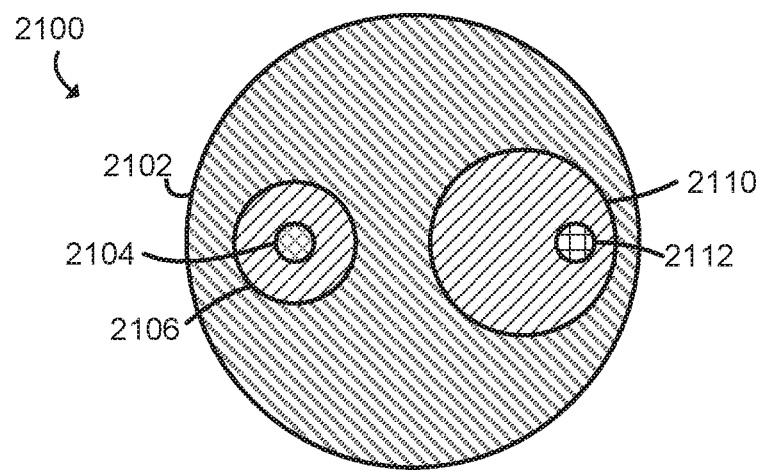
FIG. 24 is a transverse cross-section view of a fiber after the capillary breakup of FIG. 21.

It should be appreciated that the fiber 1400 shown in FIGS. 14-20 is one possible embodiment of a fiber manufacturing process, but other processes are possible as well. For example, referring now to FIG. 21, a fiber 2100 may be formed in a similar manner using the fiber draw system 1000. The fiber 2100 has an outer cladding 2102, a first inner cladding 2106, a first core sacrificial core 2108, and a first sacrificial core 2108. The fiber 2100 also has a second inner cladding 2110, a second core 2112, a hollow core 2116, and two additional sacrificial cores 2114, as shown in FIG. 22 and the top half of FIG. 21. The sacrificial core 2108 is embodied as a cyclic-olefin copolymer doped with carbon nanotubes or carbon-black (graphite) particle. As the fiber 2100 passes through the heating element 2118, the sacrificial cores 2108, 2114 break up, forming balls 2120 and 2122. It should be appreciated that the balls 2120 are conductive due to the presence of the carbon nanotubes or carbon-black.

After the sacrificial cores 2114 are broken up, a solvent such as oleic acid can be passed through the hollow channel 2216, dissolving the balls 2122. After the balls 2122 are removed, the fiber 2100 has a similar or the same structure as the fiber 500 discussed above.

While the disclosure has been illustrated and described in detail in the foregoing drawings and description, the same is to be considered as exemplary and not restrictive in character, it being understood that only illustrative embodiments thereof have been shown and described and that all changes and modifications that come within the spirit of the disclosure are desired to be protected.

The invention claimed is:

1. A fiber comprising:
a first core extending along an axis of the fiber;
a second core extending along the axis of the fiber different from the first core;
a cladding surrounding the first core and the second core;
wherein the cladding has a plurality of outlets spaced-apart along the axis of the fiber, wherein each outlet of the plurality of outlets exposes the first core or the second core to an environment surrounding the fiber,
wherein the first core and the second core generate an electric field in the environment surrounding the fiber.

2. The fiber of claim 1, wherein the first core and the second core generate the electric field in the environment surrounding the fiber based on an electrochemical interaction between the first core and the second core.

3. The fiber of claim 2, wherein the first core is zinc and the second core is silver.

4. The fiber of claim 1, wherein an external voltage source is applied across the first core and the second core to generate the electric field.

5. The fiber of claim 1, wherein the cladding is polycarbonate.

6. The fiber of claim 1, wherein the fiber is used as a suture in a wound of a patient.

7. The fiber of claim 1, wherein the electric field is at least ten millivolts per millimeter.

8. The fiber of claim 1, wherein the first core is formed of a first material, the second core is formed of a second material different from the first material of the first core, and wherein the electric field is generated between the first core and the second core in the environment surrounding the fiber based on an electrochemical interaction between the first core and the second core.

9. The fiber of claim 8, wherein the first material of the first core is zinc and the second material of the second core is silver.

10. The fiber of claim 8, wherein the cladding is polycarbonate.

11. The fiber of claim 8, wherein the fiber is used as a suture in a wound of a patient.

12. The fiber of claim 8, wherein the electric field is at least ten millivolts per millimeter.

13. The fiber of claim 8, wherein the first core is circumferentially enclosed by the cladding at axial positions offset from the plurality of outlets, and wherein the second core is circumferentially enclosed by the cladding at the axial positions offset from the plurality of outlets.

14. The fiber of claim 8, wherein the first core, the second core, and the plurality of outlets are aligned with one another relative to a plane extending through the fiber.

15. The fiber of claim 8, wherein the plurality of outlets are spaced-apart along the axis with a preset distance between each of the plurality of outlets.

16. The fiber of claim 1, wherein the first core is circumferentially enclosed by the cladding at axial positions offset from the plurality of outlets, and wherein the second core is circumferentially enclosed by the cladding at the axial positions offset from the plurality of outlets.

* * * * *